United States Patent [19]
Fatemi

[11] Patent Number: 4,961,210
[45] Date of Patent: Oct. 2, 1990

[54] HIGH RESOLUTION TECHNIQUE AND INSTRUMENT FOR MEASURING LATTICE PARAMETERS IN SINGLE CRYSTALS

[75] Inventor: Mohammad Fatemi, McLean, Va.

[73] Assignee: The United States of America as represented by the Secretary of the Navy, Washington, D.C.

[21] Appl. No.: 486,324

[22] Filed: Feb. 28, 1990

[51] Int. Cl.⁵ ................. G01N 23/207; G01N 23/203; G01N 23/201
[52] U.S. Cl. ....................................... 378/73; 378/76; 378/77; 378/81; 378/86
[58] Field of Search ...................... 378/73, 76, 77, 79, 378/81, 86, 71

[56] References Cited

U.S. PATENT DOCUMENTS 4,696,024  9/1987  Pesch ..................................... 378/71
4,710,259  12/1987  Howe et al. .......................... 378/73

FOREIGN PATENT DOCUMENTS 0842519  6/1981  Australia ............................... 378/73

Primary Examiner—Janice A. Howell
Assistant Examiner—Don Wong
Attorney, Agent, or Firm—Thomas E. McDonnell; George Jameson

[57] ABSTRACT

A method of measuring the lattice parameter in an unknown single crystal by comparing its diffraction angle to a standard single crystal, on a double-crystal diffractometer is disclosed. The method comprises several steps including mounting the unknown and standard crystals on a mounting block of the second stage of a double-crystal diffractometer aligning a tilt axis of the crystal surface with an x-ray beam and the azimuth axis of the second stage crystal mount, rotating the mounting block until the normals of the crystals have equal vertical components, tilting the crystal about the azimuth axis until the crystal normals are in line with the x-ray beam measuring the angle of the sharpest diffraction peak from each crystal while moving the crystals laterally across the beam, rotating the crystal mounting block assembly by 180 degrees about the azimuth axis while maintaining the relative tilt between the two wafers, such that the same area of the crystal surface remains in the x-ray beam during the 180 degrees rotation, sequentially measuring the angle of sharpest diffraction peak of both crystals after rotation, and calculating the diffraction angle of the unknown crystal from the standard crystal diffraction angle by using the diffraction angles measured before and after rotation by 180 degrees and thereby removing any misorientation of the crystal normals in the horizontal plane. A novel device for performing the tilt corrections of the crystals is also disclosed.

7 Claims, 6 Drawing Sheets

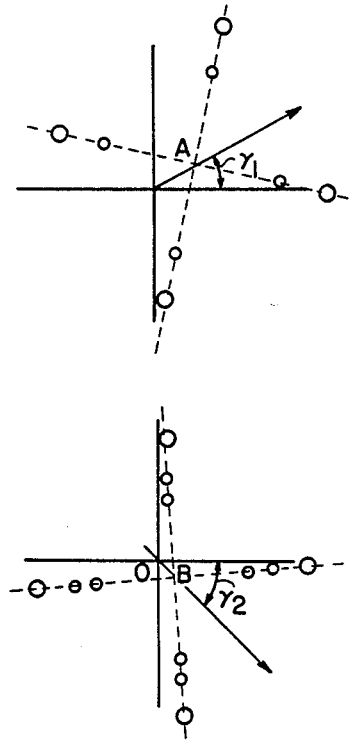
FIG. 4A
FIG. 4B
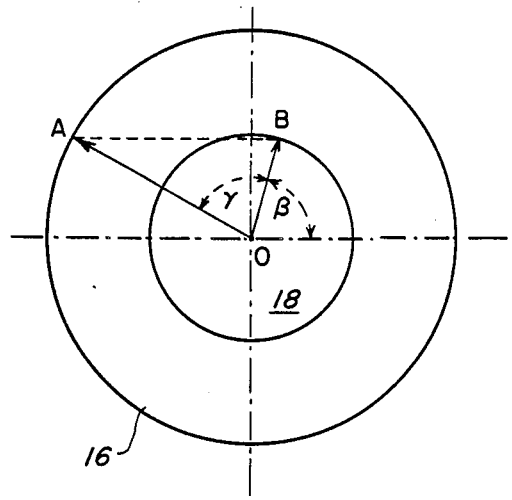
FIG. 5

HIGH RESOLUTION TECHNIQUE AND INSTRUMENT FOR MEASURING LATTICE PARAMETERS IN SINGLE CRYSTALS

BACKGROUND OF THE INVENTION

1. Field Of The Invention

This invention relates to an improved double-diffractometer for the precise measurement of lattice parameters in single crystal wafers, and more particularly to a technique for eliminating tilt misalignment between two independent single crystals where one crystal is misoriented in an arbitrary direction with respect to the other crystal, prior to comparing their diffraction angles.

2. Background Description

The precise measurement of lattice parameters in single crystals is important in at least two areas of research. In electronic applications, this information is used in fabricating epitaxial thin films of $Ga_{1-x}Al_xAs$ on GaAs as well as $Ga_{1-x}Al_xAs$ on $Ga_{1-7}In_4As$, and $In_xGa_{1-x}As$ on InP. These formations require exact knowledge of the substrate lattice parameter, since often a comparison with the substrate yields an accurate measure of the epilayer lattice parameter and hence a measure of the alloying content. The control of alloying content is essential in preparing lattice-matched layers and thin films useful for proper operation of microelectronic devices. In materials science, on the other hand, information on lattice parameters is used for investigating the mechanical and optical properties of materials and their variation as an indicator of the defect structure and strain. A simple measurement method, sufficiently sensitive to small variation in the lattice parameter would therefore be desirable.

During the last three decades several techniques using x-ray diffraction have been introduced which provide accuracies varying from one one-hundredth of an angstrom (0.01Å) to 0.00001Å. Most recent applications of such measurements have required the upper levels of resolution, i.e., better than .001Å, where the effects of strain and doping can be quantified as a function of minute changes in the lattice parameter. The most well known of these is the Bond method, as described in *Acta Cryst.*, 13 (1960) 814, by W. L. Bond, which permits absolute measurement of diffraction angles from which the lattice parameter may be calculated. This technique, while in principle is unsurpassed for its accuracy has nevertheless several drawbacks, one of which is the complexity and the bulk of the instrumentation which relies on a very accurate and therefore expensive theta circle for positioning the crystal. The second is the relatively long measurement time and the difficulties associated with automation which reduce this time to only about 30 minutes per measurement. The third drawback is that to attain the part-per-million accuracy the samples must be perfect over a relatively wide area. Although this last condition is necessary for all high resolution measurements, it is not a condition which can be satisfied for most crystals of interest under development today. Thus, the state of perfection of most present-day crystals, except for Si and Ge, is such that the resolution required for their evaluation need not exceed a few ten parts per million. Rather, changes in the lattice constant corresponding to the fourth decimal place ($\sim 2 \times 10^{-4}$Å) are sought. Such variations correspond to accuracies of the order of a second of arc in the Bragg angle $\theta$. As a result, the Bond method remains an "umpire" method with principal applications in studies involving a limited number of crystals such as Si and Ge.

In addition to the Bond method, several other techniques have been introduced, all of which require specialized instrumentation without wide applicability to different materials. For example, multiple detectors, multiple sources, or specifically shaped reference crystals are used, all of which limit the application to the measurement of the variation of the lattice parameter rather than the actual parameter itself.

FIG. 1 is a perspective view of the basic structure of a typical double crystal diffractometer, such as Blake's, having two crystal stages 10 and 12. The first crystal 10 and the second crystal 12 are the main components and each of them is very accurately aligned. X-rays come from an x-ray source 14 and become partially collimated by slits $S_1$ and $S_2$ and strike the first crystal 10. Slit $S_2$ is positioned between the second crystal 12 and a detector 15. Slit $S_2$ is sometimes used in place of slit $S_2$. Both slits simply limit the beam so that it doesn't scatter. However, it is preferred to have both slit $S_1$ and slit $S_2$ near the x-ray source so that right away the total radiation is reduced to reduce the hazard of exposure. The crystals 10 and 12 have tilts $\delta_1$ and $\delta_2$ respectively between their normals n1 and n2 and a the horizontal plane, and the slant angle between the line connecting the slits $S_1$ and $S_2$ and the horizontal plane which create errors in the measurement of lattice parameters. Here the first crystal 10 is adjusted so that it can pick out diffraction angles near the characteristic radiation of the x-ray source 14—and then a characteristic radiation is reflected toward the second crystal 12. The second crystal 12 is the one which would ordinarily be in a usual double crystal diffractometer being tested. HoWever in the method proposed below in the preferred embodiment, two independent crystals take the place of the second crystal 12, i.e. a reference and an unknown crystal—both mounted in the same general area. One is translated into the x-ray beam and then the other one is translated into the beam while looking at their different diffraction angles. And by measuring the difference in diffraction angles of these two independent crystals one can calculate, by Bragg's law, the lattice parameter of the unknown crystal.

In what follows, we will first review the method as applied to a system of two independent crystals each having only a negligible component of vertical tilt. The effects of second crystal tilt and other geometrical constraints are then discussed.

Consider two crystals, C1 and C2 (unknown and standard), mounted together on the second stage of a double crystal diffractometer as shown in FIGS. 2A and 2B. The diffracting planes are assumed to be vertical, i.e., their normals, having a small misorientation angle o between them, are directed in the horizontal plane. Monochromatic X-rays arriving from the first crystal are diffracted sequentially from crystal C1 and crystal C2 by rotating the second stage. FIGS. 2A and 2B is a sketch of such an experiment in which, for the sake of simplicity, the X-ray beam—rather than the stage—is rotated. The separation between the two X-ray beams is an angle X containing both the difference in the Bragg angles $\Theta_{B1} - \Theta_{B2} = \Theta_B$, and a misorientation angle $\alpha$. In FIG. 2A, crystal C1 is shown closer to the X-ray source than crystal C2. The relationship between X, $\alpha$, and $\Theta$ is thus $$X_a = \Delta\Theta_B + \alpha. \quad (1)$$

If now the entire assembly were rotated about a horizontal azimuth axis by 180°, as in FIG. 2B, the roles of crystal C1 and crystal C2 would be interchanged, and a new quantity $X_b$ would be measured such that $$X_b = \Delta\theta_B - \alpha. \quad (2)$$

For both FIGS. 2A and 2B, angle X is the separation between two relatively sharp diffraction peaks resulting from the "parallel" geometry. Thus both $\Theta$ and $\alpha$ can be calculated from (1) and (2):

$$\Delta\Theta = (X_a + X_b)/2, \quad (3)$$

$$\alpha = (X_a - X_b)/2. \quad (4)$$

Relations (3) and (4) are valid for all configurations of independent crystals C1 and C2 with negligible vertical tilt, i.e. their normals lie in the horizontal plane, provided the algebraic signs of angles $X_a$ and $X_b$ are also taken into account.

Although these relations were introduced more than two decades ago, no applications of the concept to two independent crystals, where one crystal is misoriented in an arbitrary direction with respect to the other, have been reported. The absence of published work in this area is probably due to the fact that the double crystal diffractometer is commonly thought to be suitable only for relative angular measurements on "coherent" epitaxial growths and those related to small grain boundary strains in one crystal alone. In these cases, most uncertainties associated with the double crystal alignment would nearly vanish due to the cancellation of instrumental factors common between two parts of the crystal, especially if adjustments other than the angle $\Theta$ were unnecessary. On the other hand, if a significant readjustment of the diffractometer were needed, such as in transition between two independently mounted crystals, the simple relationship among the parameters of eqs. (3) and (4) would no longer hold.

Mathematical analyses and supporting experiments reported by various workers show that aside from influencing the breadth of the rocking curve, the non-zero relative tilt between the first and second crystal, C1 and C2, appears as a measurable shift in the diffraction angle $\Theta$. Since it is not unusual for any given crystal to be generally misaligned by 1°–2°, an experimental difficulty arises in that as one crystal is tilted into the optimum diffracting position, the other may be tilted out, and vice versa. Presumably, then, one approach to removing the errors would be to alternately correct the tilt of each wafer before measuring its rocking curve. The procedure, however, would prove unsatisfactory due to the fact that any intermediate disturbance of the tilt mechanism would introduce significant errors (typically a few seconds of arc) in the ultimate difference $\Delta\Theta_B$. In short, sequential adjustment of the tilt for two wafers does not provide a highly accurate means of comparing their diffraction angles. The difficulty in comparing two arbitrarily mounted crystals arises from the fact that the measured diffraction angle $\Theta$ is a combination of the Bragg angle $\Theta_B$, geometrical and instrumental parameters and errors of tilt and misalignment. For an analysis of the errors in measurement of the diffraction angles due to the tilt, See "A High-Resolution Double-Crystal Diffractometer Method For The Measurement Of Lattice parameter In Single Crystals", *J. of Crystal Growth*, 96 (1989) 318–320 by M. Fatemi et al. Thus, a direct application of eqs. (3) and (4) without considering the tilt differences between the two wafers C1 and C2 would lead to erroneous results.

SUMMARY OF THE INVENTION

Accordingly, it is a general object of the present invention to compare the lattice parameter of an unknown crystal to a standard crystal.

It is a more specific object of the present invention to compare the lattice parameters of two independent crystals (standard and unknown), where one crystal is misoriented in an arbitrary direction with respect to the other.

It is another object of the present invention to provide a simple method and instrument for comparing the diffraction angles of two independent crystals, at only two azimuths of 0° and 180° without introducing tilt errors.

It is a further object of the present invention to provide a simple, inexpensive, and rapid alternative to Bond's method in applications where typical resolutions of 10-20 ppm are acceptable, but where, in addition, resolutions of the order of 1 ppm are potentially attainable.

The foregoing objects are accomplished by a novel method of measuring the lattice parameter in an unknown single crystal by comparing its diffraction angle to a standard single crystal, on a double-crystal diffractometer. The method comprises several steps including mounting the unknown and standard crystals on a mounting block of the second stage of a double-crystal diffractometer such that a tilt axis of the crystal surface is in line with an x-ray beam and the azimuth axis of the second stage crystal mount, rotating the mounting block until the normals of the crystals have equal vertical components, tilting the crystals about the azimuth axis of the mounting block until the crystal normals lie in the horizontal plane in line with the x-ray beam, such that the same point on the crystal surface remains fixed in the x-ray beam, sequentially measuring the angle of the sharpest diffraction peak from each crystal while moving the crystals laterally across the beam, rotating the crystal mounting block assembly by 180 degrees about the azimuth axis while maintaining the relative tilt between the two wafers, such that the same area of the crystal surface remains in the x-ray beam during the 180 degrees rotation, sequentially measuring the angle of sharpest diffraction peak of both crystals after rotation, and calculating the diffraction angle of the unknown crystal from the standard crystal diffraction angle by using the diffraction angles measured before and after rotation by 180 degrees and thereby removing any misorientation of the crystal normals in the horizontal plane.

BRIEF DESCRIPTION OF THE DRAWINGS

A more complete appreciation of the invention will be readily obtained by reference to the following Description of The Preferred Embodiment and the accompanying drawings wherein:

FIGS. 4A and 4B show a schematic example of a typical pair of Laue back reflection patterns obtained sequentialy from two crystals attached to a single mounting block;

FIG. 5 shows an analysis of misorientations from the Laue patterns of FIGS. 4A and 4B;

DESCRIPTION OF THE PREFERRED EMBODIMENT

Figure 1:
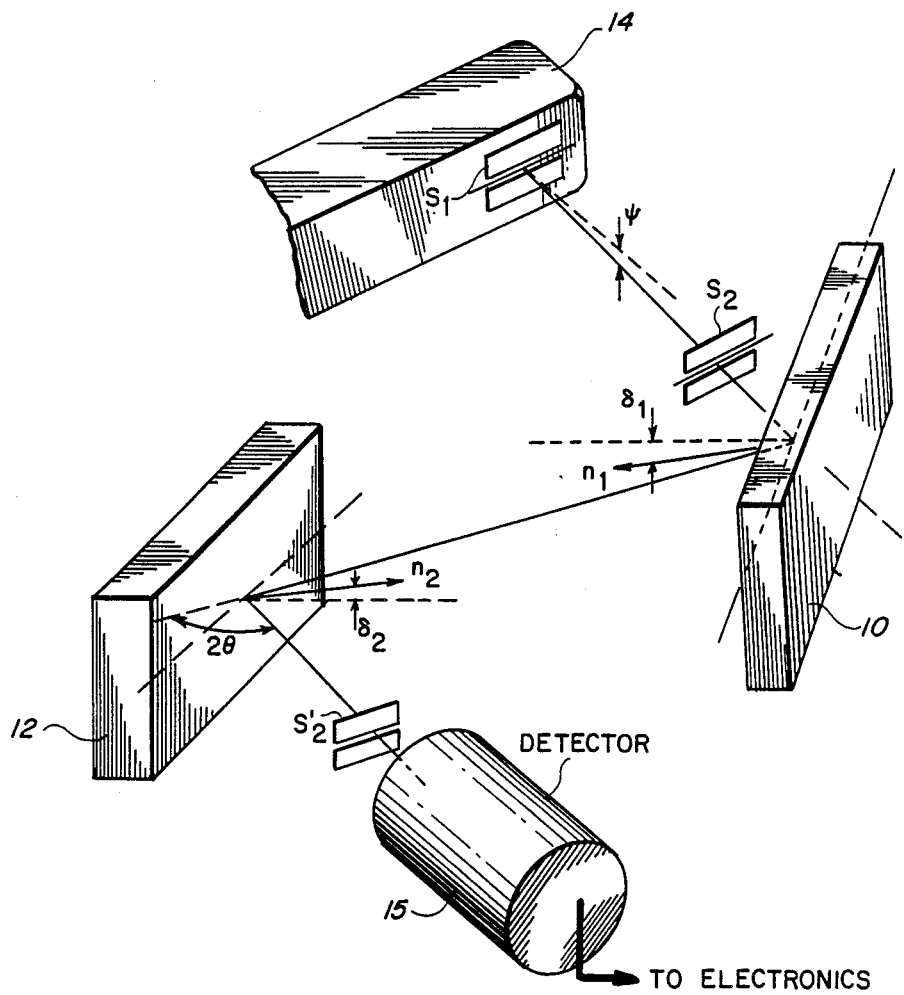
FIG. 1 is a perspective view of the basic structure of a typical double crystal diffractometer.
Figure 2A:
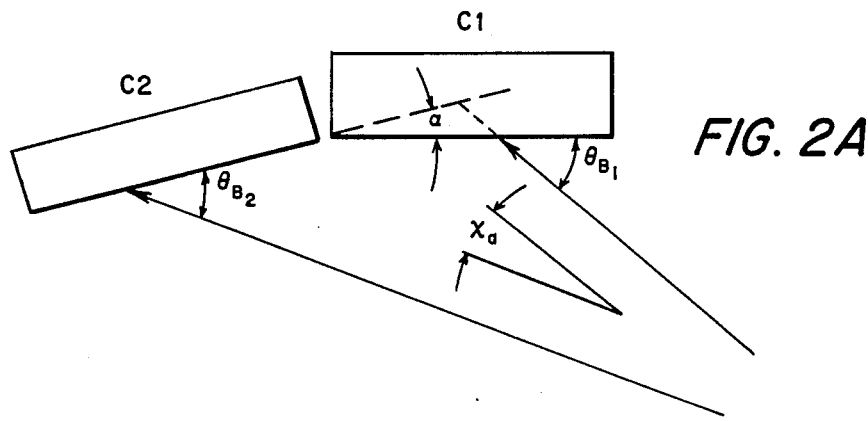
FIG. 2(A-B) show configurations of two independent crystals C1 and C2 having negligible vertical tilt and with a misorientation angle $\alpha$ between their normals in the horizontal plane.
Figure 2B:
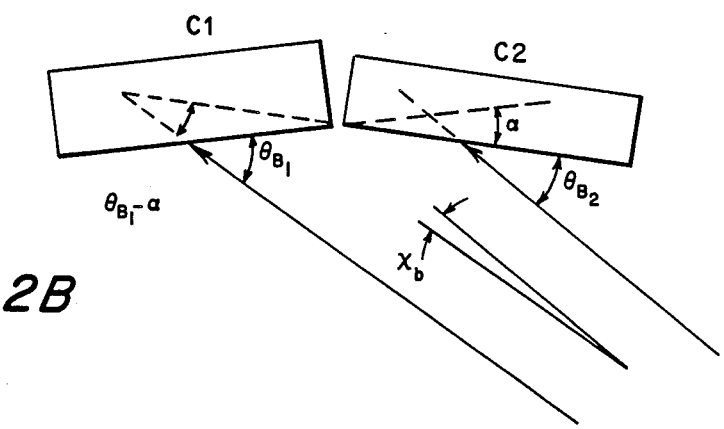
Figure 3A:
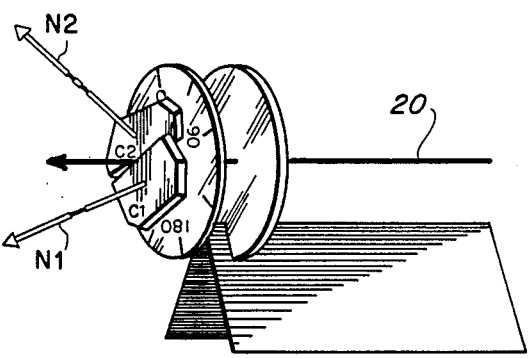
FIGS. 3(A–C) show a redrawing from an original model constructed as a training aid in visualizing the tilt angles under various configurations.
Figure 3B:
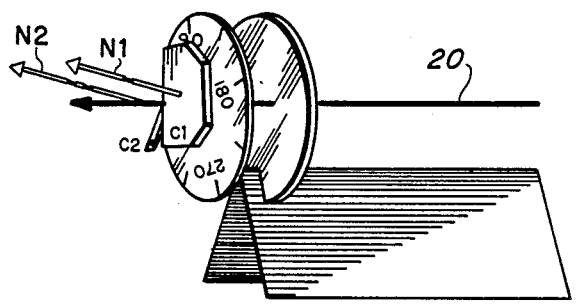
Figure 3C:
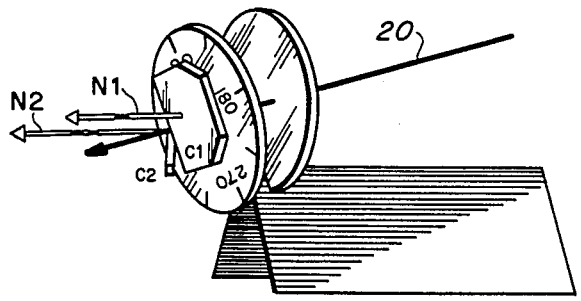

A novel method for simultaneous equalization of the tilts of both crystals C1 and C2 mounted on the second stage of a double-crystal diffractometer is now described. FIGS. 3(A–C) show a redrawing from an original model constructed as a training aid in visualizing the tilt angles under various configurations—here, it is viewed along a horizontal line of sight. FIG. 3A shows an arbitrary configuration of the two crystals C1 and C2; crystal C2 having a positive, and crystal C1 a negative tilt, i.e. the normal N2 of crystal C2 is above the horizontal plane the normal N1 of crystal C1 is below the horizontal plane. The axis 20 of the mounting block is horizontal (black arrow) and coincides with that of the azimuth axis. In FIG. 3B, the angle of the mounting block has been rotated, until the two diffracting plane normals N1 and N2 appear parallel, although they are both oriented above the horizontal plane. This is equivalent to the statement that the unit vectors normal to the diffracting planes have equal vertical components. In FIG. 3C, a tilt correction has been applied to the mount (black arrow) until both normals N1 and N2 lie in the horizontal plane and are parallel with the normal of the first crystal stage of the double crystal diffractometer. Both crystals can now be sequentially measured for their relative rocking curve positions without the need to readjust the tilt. After the measurement, a 180° rotation (not shown) of the mount about the azimuth axis will maintain the relative tilt between the two wafers. Again, both crystals C1 and C2 are sequentially measured for their relative rocking curve positions without the need to readjust the tilt. Since the tilt errors have been corrected (crystal normals N1 and N2 both lie in the horizontal plane), Eqs. (3) and (4) can now be used to determine the diffraction angles between the crystals C1 and C2. With the lattice parameter of the known crystal, the lattice parameter of the unknown can be calculated.

To achieve the equal-tilt condition described above, the Laue back reflection technique is used, as follows. A two-crystal mounting-plate is attached to a horizontal slide and is mounted on the Laue camera, such that each wafer may be positioned into the beam without altering its orientation in space. The crystal-to-film distance is chosen considerably longer than the standard 30 mm; it is advantageous to use a distance of about 90 mm. In this fashion, the relative tilts of the two crystal wafers C1 and C2 become proportionately magnified and can be measured more precisely. FIGS. 4A and 4b show a schematic example of a typical pair of Laue back reflection patterns obtained sequentialy from two crystals attached to a single mounting block (dimensions exaggerated for clarity). Two such X-ray patterns are completed in approximately 15 min. The analysis of misorientations is shown with the aid of FIG. 5. The distances OA and OB between the zone axes and the film centers are measured with a ruler and with the aid of a magnifying glass, and are used as radii of two concentric circles 16 and 18 respectively, shown in FIG. 5. The circles 16 and 18 define the loci of the pole axes which would be swept if the crystal mount were to rotate in its own plane. During this rotation, by any amount, the angle $\delta_1 + \delta_2$ between the poles would remain constant. What is sought is a configuration in which both poles lie along the same latitude either above or below the equatorial line.

In FIG. 5, if $\beta$ is the angle between the final direction of $R_2$ and the equator, where $OA = R_1$, $OB = R_2$, and $<(AOB) = \gamma_1 + \gamma_2 = \gamma$, we get $R_1 \sin(\gamma + \beta) = R_2 \sin \beta$. (11)

This equation can be solved for $\beta$ with reasonable accuracy (~0.5°) in a few minutes on a hand calculator. The angle $\beta$ is chosen such that both OA and OB terminate at the same latitude on their own circles. Thus, the two-crystal mounting block must be rotated by an angle $\beta + \gamma_2$ in the case of the two crystals having tilts shown in FIGS. 4A and 4B.

The modifications on the second crystal stage of the double crystal diffractometer is now described.

Figure 6:
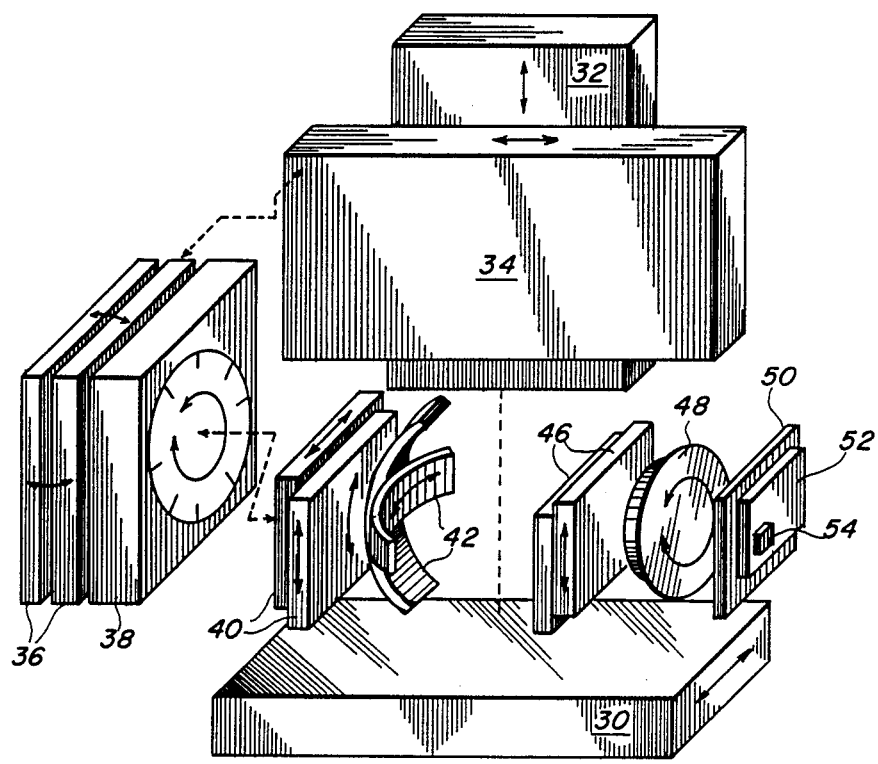
FIG. 6 is a sketch of the required components of the second stage of the double-crystal diffractometer to perform the reversal technique.

A sketch of the required components of the second stage of the double-crystal diffractometer to perform the reversal technique is shown in FIG. 6. The second stage includes a base and specimen lateral translation 30, a main height control 32, a fore-aft translation slide 34, a main tilt mechanism 36, a main azimuth control 38, specimen alignment goniometer (translation and tilt) 40 and 42, height selector slide 46, initial-azimuth alignment ring 48, and specimen mounting block 50 with a reference 52 and unknown crystal 54 attached to the mounting block 50. The design of the second stage was based on the premise of operational simplicity without introducing misalignment errors due to mechanical instability. It is for this reason that the crystal translations in both lateral and vertical directions are controlled by the first and last mechanisms, i.e the main lateral translation 30 and the vertical sample translation 46, respectively. The lateral translation stage 30 supports the entire weight of the second crystal stage of the double-crystal diffractometer and can be used to select various test points of the sample along a horizontal strip in line with the x-ray beam. On the other hand, translation along the vertical line is accomplished by the manually operated micrometer (not shown) which is attached to the vertical sample translation 46. Attached to the main lateral translation stage 30 is the main vertical slide 32. This vertical slide 32 is used in the preliminary alignment of the instrument to compensate for changes in the height of the mounted crystals 52 and 54 during the adjustments in the tilt of the omega axis by a main tilt mechanism 36. Next, the fore-aft translation stage 34, controls the position of the crystal surface in the x-ray beam. The main omega-axis control 36, is carried by the fore-aft slide 34 and supports, in turn, a motor-driven omega rotation mechanism 38. The goniometric adjustments for the second crystal stage, including both the sample-centering translation slides 40 and sample tilt controls 42 are next in line. The two components 40 and 42 are part of a commercially available motor driven eucentric goniometer which is available from Blake. Since the axes of the sample tilt controls 42 must lie in the sample surface, appropriate spacers are needed to compensate for the extra distance between the outer face of the goniometer and the tilt axes. Some of this space is taken up by the specimen mounting plate 50 and the height selector 46 used to vary the sample height. Because of the variety of sample thicknesses encountered, several spacers are usually kept on hand. It is absolutely essential that prior to any of the alignment steps described below, spacers of correct thickness are used with each wafer. We also assume that the vertical Θ-axis of the second crystal stage has already been determined, that the incident x-rays, from the first crystal stage, intersect this axis horizontally, and that the tilt center, i.e. the intersection of the two tilt axes 42 is in line with the omega axis. This last operation can usually be performed "on the bench" and requires an iterative adjustment of sample tranlations 40 and rotation about the omega axis. Incorporating these components ensures that the measured area of each crystal 52 and 54 remains in the X-ray beam, both during the tilt adjustment and after azimuthal rotation by 180° as described above.

It is essential to equip the second stage of the double-crystal diffractometer with two sets of tilts, one of which the main tilt 36 remains untouched after the initial alignment of the spectrometer, while the specimen tilt 42 in front, is used to adjust the crystals for rocking curve measurements. Similarly, two sets of vertical height controls are needed; one the main height adjustment 32 is used to raise the azimuth axis to the same height as the X-ray beam, while the other height selector 46, placed in front of the specimen tilt 42, is used to bring various regions of the crystal into the beam, without displacing the tilt mechanism 42. Attached to this translation stage is an adjustable ring 48 fixing the mounting plate 50 in the desired orientation. A detailed description of these modifications is published in the Proceedings of Denver X-ray Analysis Conference, 33, Aug. 3–9, 1989, in a paper entitled "Advances in X-ray Analysis" by M. Fatemi, which paper is herein incorporated by reference.

The best mounting arrangement for the two crystals 52 and 54 is to attach the small unknown crystal 54 atop and near one corner of the standard crystal 52, such that the latter may be accessed both laterally and vertically from the direction of the unknown crystal 54. As a matter of convenience, a large (25×25×2.5 mm thick) Si reference crystal 52 has been used to support the much smaller (~4×6×0.5 mm thick) unknown crystal 54 in the experimental setup described below. The latter 54 can then be used as a secondary reference on larger wafers (presently up to 75 mm diameter).

Several alternatives for mounting and for measurement of the diffraction angles were investigated, the best method being accomplished through the arrangement shown in FIG. 6. An apparently simple arrangement, with the two wafers mounted side-by-side and illuminated simultaneously by the same X-ray beam, was also considered, but did not prove satisfactory. Specifically, consider the case in which one wafer is mounted above the other and the vertical slit is opened slightly to allow the X-ray beam to fall on adjoining areas of both crystals. Since the two wafers are independently mounted, an azimuthal rotation similar to that described earlier will probably be necessary. Assuming now that a rotation of about 90° is required. In the new orientation, therefore, only one of the crystals will be exposed to the beam. Furthermore, since it is important to compare the same areas of both samples as initially used in the "Laue" tilt equalization, each sample would have to be moved into the beam using both the lateral and the vertical translation stages. This unnecessary complication can be avoided by choosing the "stack" method of mounting, described above. The design of the modified second stage, based on the premise of simplicity, thus requires only that the lateral translation stage 3 be used in adjusting the beam position on each wafer. The vertical translation stage 46 is, on the other hand, quite lightweight and is thus left undisturbed once a particular region of the unknown specimen has been chosen for measurement. Clearly, the lateral translation stage 30 must be sufficiently stable and "smooth" in order to retain the angular accuracy during this motion.

A technique for the optimum mounting and positioning of each crystal in the beam is now described. It is important to ensure that, for each wafer, the same area is examined at both the 0° and 180° azimuths. This is quite easy if some precautions are taken. As part of the initial double diffractometer alignment, the X-ray beam is adjusted so that it intersects both the azimuth and the tilt axes at the same point. It is for this reason that the vertical specimen translation stage 46 is placed in front of (i.e., carried by) the tilt goniometer 40 and 42, for in this manner a horizontal "strip" of each wafer can be selected independent of the tilt setting.

Figure 7A:
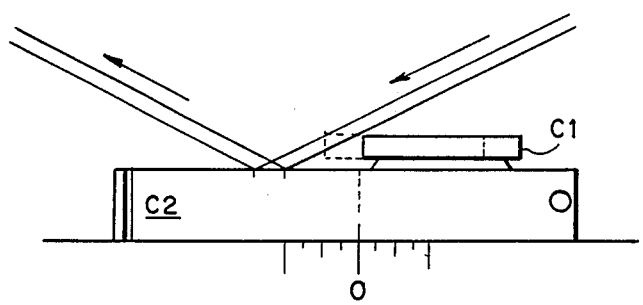
FIGS. 7A and 7B show a technique for the optimum positioning of each crystal in the beam.
Figure 7B:
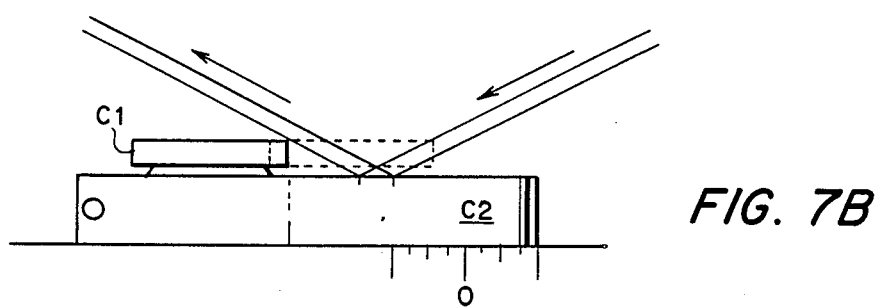

Next, it is necessary to use fiduciaries as an aid in locating a desired spot along the strip. The points on the left and right edges of the upper crystal C1 at which the diffracted intensity just vanishes can be used for this purpose as shown in FIG. 7A. All points on crystals C1 and C2 can be unambiguously chosen with these references. From FIG. 7A, it is also obvious that the measurement of crystal C2 near both edges of crystal C1 is restricted by the thickness of the latter, which stops either the incident or the diffracted beam. Keeping in mind the reversibility of the X-ray optical path and using the fiduciaries defined above, one can easily account for this offset, and ascertain that the same points on C1 and C2 are used in the measurements at both azimuths as shown in FIG. 7B. In general, X-ray beam positions can be defined with this procedure to within 0.1 mm.

Experimental Results

As a test of the method just described, the lattice parameters of several types of GaAs wafers were measured by comparing them to a perfect (FZ)-grown Si standard, in (400) reflection. Cu K$\alpha_1$ radiation monochromatized by means of a similar Si wafer was used. The total precision Θ range of about 5.5° on the Blake instrument was more than sufficient for comparing Si(Θ$_B \approx$34.563°) and GaAs (Θ$_B \approx$33.025°) allowing for a few degrees of misorientation between their diffracting planes. Among the specimens measured were the following:

1—an "undoped", Czochralski-grown commercial wafer;
2—an "undoped", wafer supporting an MBE-grown layer of GaAlAs;
3—a plain, In-doped commercial wafer;
4—an "early vintage", Cr-doped, commercial wafer used as a substrate for an MOCVD-grown layer of GaInAs.

In addition, samples #1 and #3 as well #2 and #3 were compared in pairs to check the reproducibility of the method. In all cases, the measurements listed in TABLE I below, were reproducible at least within 1 arc sec. Lattice parameters were calculated using the Si value $a_o = 5.431028 Å$.

TABLE I

| Measurement | $\Delta \Theta_B$ (arc sec) | a (Å) |
|---|---|---|
| #1 + Si | 5541.0 | 5.65351 |
| #2 + Si | 5542.5 | 5.65357 |
| #3 + Si | 5592.9 | 5.65569 |
| #4 + Si | 5551 ± 4 | 5.65393 ± 0.00017 |
| #1 + #3 | 52.6 | — |
| #2 + #3 | 50.7 | — |

The results shown in TABLE I indicate the excellent reliability of lattice parameter measurement using the proposed comparative method. This is evident from several facts. (1) The difference in lattice parameter between any two wafers (such as #1 and #3, or #2 and #3) measured indirectly, i.e., through a standard Si(100), agrees nearly exactly with that obtained by direct comparison (51.9 versus 52.6 and 50.4 versus 50.17 arc sec, respectively). (2) The fact that the lattice parameter for Indoped material is larger than the undoped, consistent with the expectations, is clearly noted. (3) The diversity of values for GaAs supports independent data that the lattice parameter in GaAs varies not only within a given sample but for different wafers as well. TABLE II below, shows some of the values quoted and used by various authors. Despite the fact that some of the variation in the values may well be due to instrumental and operator judgment, these results (showing a spread of approximately 160 ppm) indicate that computations involving lattice parameters for GaAs and AlAs must be carried out carefully. For example, the calibration factor k used in the measurement of aluminum concentration x in thin films of $Ga_{1-x}Al_xAs/GaAs$ is defined by $$\Delta \Theta_B = kx,$$

where $\Theta_B$ is the angular distance between the (400) peaks of $Ga_{1-x}Al_xAs$ and GaAs, and k 375" for Cu $K\alpha_1$ radiation. While this number was originally obtained through a direct comparison of two specific batches of bulk GaAs and AlAs, the variation in GaAs alone (i.e., without considering possible differences in AlAs) may account for an uncertainty in this calibration factor by about 24 arc sec, equivalent to approximately 7% variation in the calculated aluminum concentration. Hence, when absolute, rather than qualitative changes in aluminum x-values are sought, lattice parameter measurements should be performed for the particular GaAs and AlAs used at the time. In this context it should be noted that the variations observed for specimen #4 are almost entirely due to the inhomogeneities in the crystal rather than to the experimental technique. The large spread in these numbers is consistent with the relatively imperfect crystal, which showed rocking curve breadths of about 35 to 40 arc sec, compared to the remaining specimens which had breadths between 10 and 20 arc sec.

TABLE II

| Author/Source | $a_o(GaAs)(Å)$ |
|---|---|
| E. Estop et al. Acta Cryst., A32 (1976),627. | 5.6528 (±0.0006) |
| Sze "Physics of Semiconductor Devices", (Wiley, N.Y., 1981) p. 848. | 5.6533 |
| Kishino et al. J. Crystal Growth. 24/25 (1974) 226. | 5.6535 |
| Baker et al. Solid State Electron., 19 (1976) 331. | 5.653709 |
| PDF Powder Diffraction File Card No. 32-389 (Joint Committee on Powder Diffraction Standards, Phil., Pa, 1981). | 5.6538 |

ALTERNATIVES

Several variations in both mechanical and procedural aspects can be implemented in the technique described above. For example, the azimuth adjustment mechanism can be automated in such a way that the proper orientation (initial azimuth) is carried out immediately on the instrument rather than on a separate mount. This may be accomplished through the use of a fast optoelectronic device which would detect the misorientation of the Lauespots, rather than the present photographic method which takes about 15 minutes before the actual measurement may begin. A second improvement may be made in the translation mechanism to control the lateral positions of the two crystals C1 and C2 rather than moving the entire upper stage. Also, a crystal-broadened x-ray beam may be used which would allow the comparison of two points on the two crystal, separated by a fixed distance, so that no mechanical translation would be needed for each measurement. Finally, the azimuth rotation by 180° of the two crystals may be done much faster by choosing appropriate speed ramps using stepper or D-C motors. These modifications would help adapt the technique to industrial and large scale applications. Also, it should be obvious that once the initial alignment and orientation of the specimen is completed, the entire measurement process is easily adaptable to computer control, and can be designed in such a way that human operator involvement is minimal, thus significantly reducing the measurement time for each data point. In this disclosure, several aspects of a comparative double crystal diffractometer method for the measurement of diffraction angles were examined. The method, based on removing the tilt errors, is shown to yield a resolution which is nearly equivalent to Bond's method. However, as a comparative technique it relies on a prior absolute measurement of lattice parameter for the reference crystal. A simple procedure was described for correcting the tilt on both crystals, by which typical resolutions of 8 ppm are effortlessly obtained following relatively inexpensive improvements on a commercially available double diffractometer. In the method presented in this disclosure, the angle of diffraction from an "unknown" crystal is measured relative to a standard specimen, whose lattice parameter and diffraction angle are well known. Errors associated with relative misorientations between the unknown and standard are eliminated through a simple procedure. The system has been tested in applications similar to those enumerated in the Background of The Invention, and the results have been found reproducible to within 1 arc sec. To achieve this resolution to within 1 arc sec, it is necessary to ensure that the tilt settings for the two wafers are within about 0.1° of each other.

The present method has several attractive features, one of which is the simplicity of procedure and instrumentation. Any double-crystal diffractometer with a precise Θ range of 5°–10° can be used without the need for full-circle accuracy on either Θ or 2Θ. A second feature is the speed and economy with which secondary standards can be obtained. The data reported here were gathered on a manually-operated system at the rate of approximately one hour each, after relatively inexpensive modifications of a Blake double crystal instrument and using a novel procedure for the simultaneous alignment of both the standard and test crystals. It is estimated that an automated version of the present manual prototype will be able to perform individual measurements in about 15–20 minutes, and even faster if a series of data points on the same crystal are needed. These modifications expanded the capabilities of the instrument to other high resolution measurements. All other customary uses of the double diffractometer such as rocking curve analysis and spectrometry are also simplified with these modifications.

Obviously, many modifications and variations of the present invention are possible in light of the above teachings. It is therefore understood that within the scope of the appended claims the invention may be practiced otherwise than as specifically described.

What is claimed and desired to be secured by Letters Patent in the United States is:

1. A method of measuring the lattice parameter in an unknown single crystal by comparing said unknown single crystal's diffraction angle to a standard single crystal, on a double-crystal diffractometer, which method comprises the steps of:

mounting said unknown and standard crystals on a mounting block of the second stage of a double-crystal diffractometer such that a tilt axis of the crystal surface is in line with an x-ray beam and the azimuth axis of the second stage crystal mount;

rotating the mounting block until the normals of said crystals have equal vertical components;

tilting the crystals about the azimuth axis of the mounting block until the crystal normals lie in the horizontal plane in line with the x-ray beam, such that the same point on the crystal surface remains fixed in the x-ray beam;

sequentially measuring the angle of the sharpest diffraction peak from each crystal while moving the crystals laterally across the beam;

rotating the mounting block assembly by 180 degrees about the azimuth axis while maintaining the relative tilt between the two wafers, such that the same area of the crystal surface remains in the x-ray beam during the 180 degrees rotation;

sequentially measuring the angle of sharpest diffraction peak of both crystals after rotation which point of measurement is the same as the first sequential measurement; and calculating the diffraction angle of the unknown crystal from the standard crystal diffraction angle by using the diffraction angles measured before and after rotation by 180 degrees, thereby removing any misorientation between the respective crystal normals in the horizontal plane.

2. The method of claim 1 wherein a Laue back-reflection technique is used to determine the orientation of the tilts of the two arbitrarily mounted crystals on the mounting block prior to placing the mounting block on the second stage of the double-crystal diffractometer such that the angle of rotation about the azimuth axis, to give equal vertical components to the respective crystal normals, is determined.

3. The method of claim 1 where the unknown crystal is mounted on the surface of the standard crystal.

4. A method of removing the tilt errors between two arbitrarily mounted crystal on a mounting block comprising the steps of:

mounting an unknown crystal and a standard crystal on a mounting block such that a tilt axis of the crystal surface is in line with an azimuth axis of the crystal mount;

rotating the mounting block until the normals of the crystals have equal vertical components; and tilting the crystals about the azimuth axis of the mounting block until the crystal normals lie in the horizontal plane, such that the same point on the crystal surface remains fixed with respect to the azimuth axis of the crystal mount.

5. A device, mounted on a second stage of a double-crystal diffractometer, for removing tilt errors between two arbitrarily mounted crystals, thereby allowing measurement of the lattice parameter in an unknown single crystal by comparing its diffraction angle to a standard single crystal, on a double-crystal diffractometer, which device comprises:

a mounting block for mounting said unknown and standard single crystals;

means for positioning said mounting block of the second stage of a double-crystal diffractometer such that a tilt axis of the crystal surface is in line with an x-ray beam and the azimuth axis of the second stage crystal mount;

first rotating means for rotating the mounting block until the normals of said crystals have equal vertical components which first rotating means is behind the crystal mount;

means for tilting the crystals about the azimuth axis of the mounting block until the crystal normals lie in the horizontal plane in line with the x-ray beam, such that the same point on the crystal surface remains fixed in the x-ray beam; and second rotating means for rotating the crystal mounting block assembly by 180 degrees about the azimuth axis while maintaining the relative tilt between the two wafers, such that the same area of the crystal surface remains in the x-ray beam during the 180 degrees rotation; and means for translating the crystals laterally in the horizontal plane such that their respective diffraction peaks can be measured both prior to and after rotation by 180 degrees.

6. The device of claim 5 wherein the means for tilting the crystals about the azimuth axis comprises a goniometer.

7. A device for removing tilt errors between two arbitrarily mounted crystal on a mounting block comprising:

a mounting block for mounting an unknown crystal and a standard single crystal;

means for positioning said mounting block such that a tilt axis of the crystal surface is in line with the azimuth axis of the crystal mount;

first rotating means for rotating the mounting block until the normals of said crystals have equal vertical components which first rotating means is behind the crystal mount;
means for tilting the crystals about the azimuth axis of the mounting block until the crystal normals lie in the horizontal plane, such that the same point on the crystal surface remains fixed; and
second rotating means for rotating the crystal mounting block assembly by 180 degrees about the azimuth axis while maintaining the relative tilt between the two wafers, such that the same area of the crystal surface remains in the x-ray beam during the 180 degrees rotation; and
means for translating the crystals laterally in the horizontal plane while maintaining the crystal tilt axis stationary in the horizontal plane.

* * * * *